(12) United States Patent
Peter et al.

(10) Patent No.: US 6,355,755 B1
(45) Date of Patent: Mar. 12, 2002

(54) SYNTHESIS OF POLY(PROPYLENE FUMARATE) BY ACYLATION OF PROPYLENE GLYCOL IN THE PRESENCE OF A PROTON SCAVENGER

(75) Inventors: Susan J. Peter, Baltimore, MD (US); Laura J. Suggs, Minneapolis, MN (US); Paul S. Engel; Antonios G. Mikos, both of Houston, TX (US)

(73) Assignee: Wm. Marsh Rice University, Houston, TX (US)

( * ) Notice: Subject to any disclaimer, the term of this patent is extended or adjusted under 35 U.S.C. 154(b) by 0 days.

(21) Appl. No.: 09/678,816

(22) Filed: Oct. 4, 2000

Related U.S. Application Data

(63) Continuation of application No. PCT/US99/07912, filed on Apr. 9, 1999.
(60) Provisional application No. 60/081,308, filed on Apr. 10, 1998, provisional application No. 60/081,405, filed on Apr. 10, 1998, and provisional application No. 60/082,182, filed on Apr. 16, 1998.

(51) Int. Cl.[7] .............................................. C08F 118/00
(52) U.S. Cl. ........................ 526/320; 528/306; 523/115
(58) Field of Search ........................... 526/320; 528/306

(56) References Cited

U.S. PATENT DOCUMENTS

| | | | |
|---|---|---|---|
| 3,701,748 A | 10/1972 | Kroekel | 260/40 |
| 4,843,112 A | 6/1989 | Gerhart et al. | 523/114 |
| 4,888,413 A | 12/1989 | Domb | 142/471 |
| 5,286,763 A | 2/1994 | Gerhart et al. | 514/772.4 |
| 5,364,627 A | 11/1994 | Song | 424/443 |
| 5,420,179 A | 5/1995 | Fourquier et al. | 523/523 |
| 5,527,864 A | 6/1996 | Suggs et al. | 525/444 |
| 5,733,951 A | * 3/1998 | Yaszemski | 523/116 |
| 5,946,457 A | 8/1999 | Plate et al. | 514/772.1 |
| 5,986,043 A | 11/1999 | Hubbell et al. | 528/354 |
| 5,989,579 A | 11/1999 | Darouger et al. | 424/427 |
| 5,998,362 A | 12/1999 | Feng et al. | 514/2 |
| 6,028,164 A | 2/2000 | Loomis | 528/354 |
| 6,071,982 A | 6/2000 | Wise et al. | 523/113 |
| 6,124,373 A | 9/2000 | Peter et al. | 523/116 |
| 6,153,664 A | 11/2000 | Wise et al. | 523/115 |

* cited by examiner

Primary Examiner—Paul R. Michl
(74) Attorney, Agent, or Firm—Conley, Rose & Tayon, P.C.

(57) ABSTRACT

High molecular weight linear poly(propylene fumarate) having a relatively low polydispersity index by utilizing a relatively pure intermediate and a method for making same. Fumaryl chloride and propylene glycol are reacted in the presence of potassium carbonate. The potassium carbonate present in the reaction solution prevents the acid by-product from catalyzing reactions at the fumarate double bond. The bis(propyl fumarate) produced according to this technique can be transesterified using conventional processing steps to yield P(PF). The P(PF) produced from bis(propyl fumarate) produced according to the present method has a higher molecular weight and is purer than P(PF) produced using previously known techniques.

22 Claims, 6 Drawing Sheets

Poly(Propylene Fumarate)

SYNTHESIS OF POLY(PROPYLENE FUMARATE) BY ACYLATION OF PROPYLENE GLYCOL IN THE PRESENCE OF A PROTON SCAVENGER

CROSS-REFERENCE TO RELATED APPLICATIONS

This is a continuation of International Application PCT US99/07912, with an international filing date of Apr. 9, 1999 which claims the benefit of provisional applications Ser. No. 60/081,308, filed Apr. 10, 1998 and entitled Synthesis of Poly(Proplyene Fumarate) by Acylation of Propylene Glycol in the Presence of a Proton Scavenger; Ser. No. 60/082,182, filed Apr. 16, 1998 and entitled In Vivo Degradation of a Poly(Propylene Fumarate)/β-Tricalcium Phosphate Injectable Composite Scaffold; and Ser. No. 60/018,405, filed Apr. 10, 1998 and entitled Crosslinking Characteristics of an Injectable Poly(Propylene Fumarate)/βTricalcium Phosphate Past and Mechanical Properties of the Crosslinked Composite for Use as a Biodegradable Bone Cement.

STATEMENT REGARDING FEDERALLY SPONSORED RESEARCH OF DEVELOPMENT

This work was funded by the National Institutes of Health AR44381 (AGM) and National Institutes of Health Biotechnology Training Grant GM08362.

TECHNICAL FIELD OF THE INVENTION

This invention relates to methods for the synthesis of high molecular weight forms of poly(propylene fumarate) having a relatively low polydispersity index. More particularly, the present invention provides methods for synthesizing poly (propylene fumarate) having molecular weights above 4,000 and polydispersity indices below 2, and more particularly below 1.8, wherein the high molecular weight poly (propylene fumarate) is synthesized in the presence of a proton scavenger.

BACKGROUND OF THE INVENTION

It is often desired to replace or reconstruct all or a portion of a living bone, such as when a bone has been broken or has been resected as a result of a bone tumor. In these instances, the missing bone can be replaced with a mechanical device, such as a pin, plate or the like, or it can be replaced with an implant that is designed to more closely resemble the original bone itself. Often these implants comprise biodegradable compounds or parts made from such compounds. For example, it is known to provide porous, biodegradable compounds that contain or are coated with an osteogenic substance. It is contemplated that bone tissue will grow back into the pores of the implant and will gradually replace the entire implant as the implant itself is gradually degraded in the in vivo environment.

For obvious reasons, implants, regardless of whether they are biodegradable, should be biocompatible and non-toxic. Furthermore, the steps required for implantation of the implant (eg. the application or generation of heat and the generation of chemical by-products) should also be biocompatible and non-toxic. Also, the techniques and time periods required for implantation should be suited to the surgical environment.

Under current practices, bone implants are typically formed from a substance that is initially malleable and then becomes hard after a reasonably short period of time. Because living bone tends to atrophy and degrade in the absence of compressive stress, however, it is important that the implant not become too hard. An implant whose compressive strength is too great (i.e. an implant that is too hard) will cause stress shielding of the surrounding bone. Stress shielding in turn causes the surrounding bone to weaken and may ultimately result in catastrophic failure. Hence, the suitability of a given substance for implantation as a bone replacement depends on its biocompatibility, set time, biodegradability and ultimate compressive strength. Certain polymers have been found to be suitable in this regard.

Poly(propylene fumarate) (hereinafter "P(PF)") is one such substance. P(PF) is an unsaturated linear polyester that degrades in the presence of water into propylene glycol and fumaric acid, degradation products that are cleared from the human body by normal metabolic processes. Although P(PF) is a known polymer, its routine, reproducible synthesis and the synthesis of high molecular weight forms and forms with low polydispersity indices have not previously been successfully accomplished. Known methods for the synthesis of P(PF), for example by equilibrium polycondensation, utilize reactions that are difficult to control. These synthetic methods typically require extremely high heat, the presence of a catalyst, and/or long reaction times.

Nevertheless, the fumarate double bonds in P(PF) are reactive and crosslink at low temperatures, making it valuable as an in situ polymerizable biomaterial. An effective composite mixture incorporating P(PF), a crosslinking monomer (N-vinyl pyrrolidinone), a porogen (sodium chloride), and a particulate phase (β-tricalcium phosphate) can be injected into skeletal defects of irregular shape or size. As is known in the art, the mechanical properties of the cured material can be tailored by altering the ratios of the porogen and particulate phase, as well as the monomer to polymer ratio.

The maximum molecular weight $M_w$ of the P(PF) polymer that has heretofore been reasonably achievable without encountering an unacceptably high polydispersity index is limited to less than 3,000. P(PF) polymers have been produced having $M_w$ above 3,000, but because the degree of cross-linking varies greatly within the specimen, the polydispersity indices, (the ratio of weight average molecular weight to number average molecular weight), for these polymers are well above 2.0. Premature crosslinking of the polymer often limits the linear size or molecular weight of the linear polymer that can be achieved. It is believed that this is in part due to the fact that some of the fumarate double bonds are reaction sites for the acid-catalyzed addition of various other groups. The presence of these groups and the corresponding elimination of the double bond reduces the degree of unsaturation and thus limits molecular weight. Early attempts to mitigate this effect and increase the weight average molecular weight entailed the use of an amine to neutralize the acid, but results of this reaction were undesirable. Other early attempts included the use of buffers, and several other materials also proved ineffective.

Hence, it is highly desirable to provide an efficient, controlled synthetic reaction whereby high molecular weight linear poly(propylene fumarate) having a relatively low polydispersity index can reproducibly synthesized without regardless of whether an acid catalyst is used.

BRIEF SUMMARY OF THE INVENTION

The present invention provides a method for making high molecular weight linear poly(propylene fumarate) having a relatively low polydispersity index by utilizing a relatively pure intermediate. According to the present invention, fumaryl chloride and propylene glycol are reacted in the presence of potassium carbonate, which serves as a proton scavenger, to produce bis(propyl fumarate). The reaction of fumaryl chloride and propylene glycol also produces HCl. The potassium carbonate present in the reaction solution reacts with the HCl to give water and $CO_2$ and prevents the acid from catalyzing reactions at the fumarate double bond. According to a preferred embodiment, a mole ratio of $K_2CO_3$ to fumaryl chloride of between approximately 1.2:1 and 3:1 is used. The bis(propyl fumarate) produced according to this technique can be transesterified using conventional processing steps to yield P(PF). The P(PF) produced from bis(propyl fumarate) produced according to the present method has a higher molecular weight and is purer than P(PF) produced using previously known techniques.

BRIEF DESCRIPTION OF THE DRAWINGS

For an introduction to the detailed description of the preferred embodiments of the invention, reference will now be made to the accompanying Figures, wherein.

DETAILED DESCRIPTION OF THE PREFERRED EMBODIMENTS

It has been discovered that the P(PF)s formed according to the preferred embodiment have greater molecular weights than those produced by previously known reaction methods without requiring the use of a catalyst. Equally importantly, the preferred method yields P(PF)s having polydispersity indices, or PI ($PI=M_w/M_n$ where $M_w$ is the weight average molecular weight and $M_n$ is the number average molecular weight), less than 2 and more preferably approximately 1.

Figure 1:
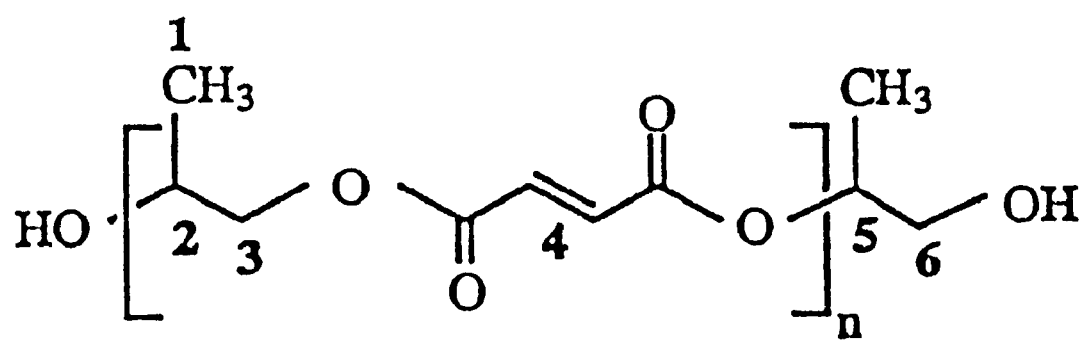
FIG. 1 is a labeled chemical structure of poly(propylene fumarate)

Referring initially to FIG. 1, the chemical structure for the desired reaction product P(PF) is shown and various functional groups are labeled 1–6. The structure depicted in FIG. 1 is confirmed by the peaks labeled correspondingly 1–6 in FIGS. 4A–C, as described in detail below. According to the present invention, $P(PF)_n$, for which n equals at least 10 and more preferably at least 14, can be manufactured consistently and with a relatively high polydispersity index in a two-step process. The first step includes acylation of propylene glycol with fumaryl chloride in the presence of a proton scavenger. As generally disclosed in U.S. Pat. No. 5,733,951, which is incorporated herein in its entirety, the acylation step releases 2HCl, which results in a lowering of the pH of the reaction solution. In prior art processes, the presence of the acid allowed the acid-catalyzed addition of various other groups, such as excess propylene glycol, at the fumarate double bond. These undesired side reactions reduced the purity of the desired bis(propyl fumarate) intermediate and thus increased the polydispersity index and reduced the maximum molecular weight of the ultimate P(PF) product that can be obtained.

It has been discovered that the addition of potassium carbonate to the reaction solution effectively neutralizes the acid and prevents premature loss of the fumarate double bond. The potassium carbonate is preferably added in molar excess, to ensure that the acid catalysis of bonding across the double bonds is minimized. This process produces a low molecular weight oligomer, bis(propyl fumarate), which can then be transesterified according to known techniques.

Figure 2:
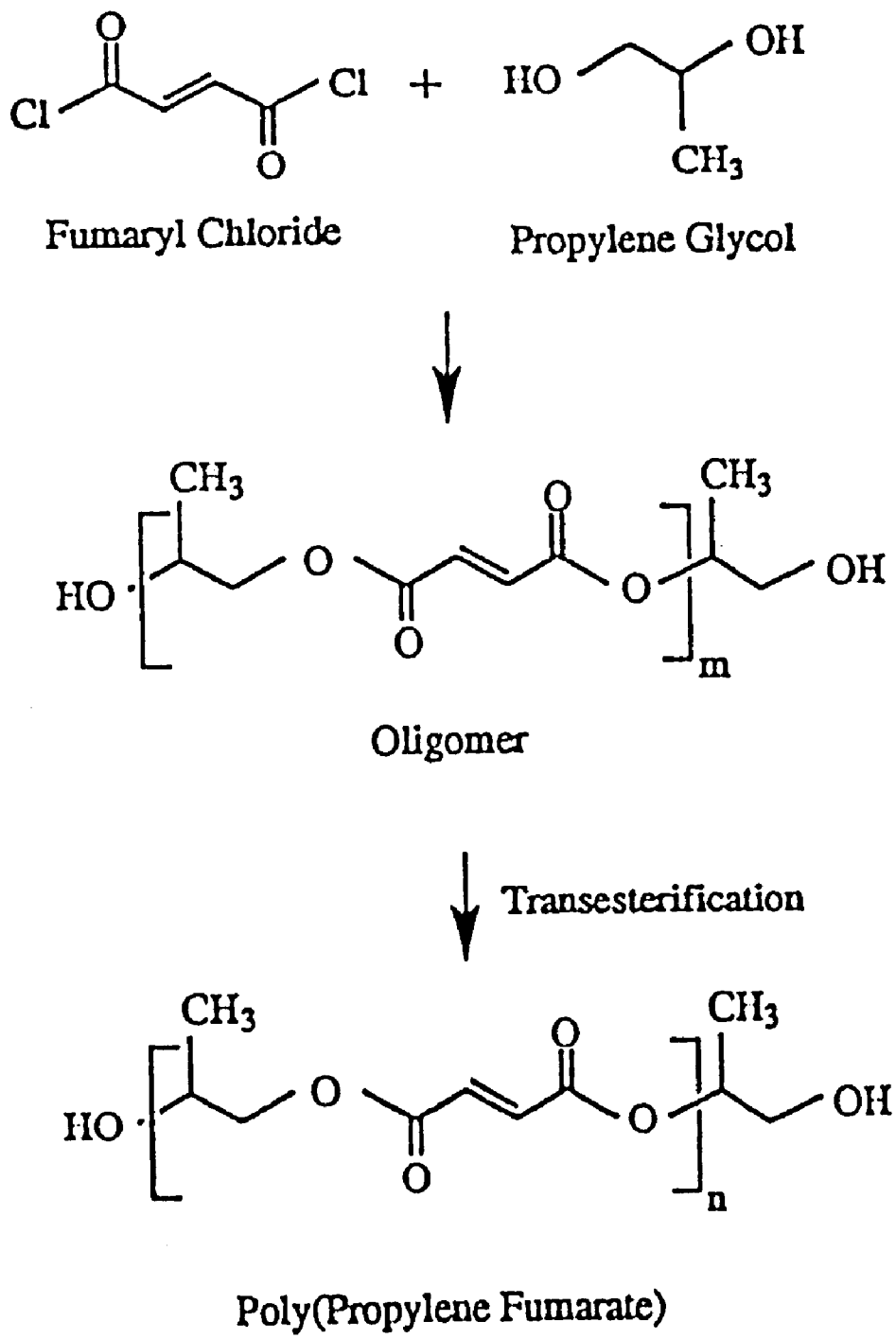
FIG. 2 is a two-step reaction scheme for the formation of poly(propylene fumarate) from propylene glycol and fumaryl chloride.

As shown in FIG. 2, the formation of PPF is a two-step reaction process. The first step involves forming a short chain oligomer from fumaryl chloride and propylene glycol in the presence of potassium carbonate. This is followed by a transesterification step to form the high molecular weight polymer, PPF. The specifics of each reaction are described below.

EXAMPLE 1

Materials Fumaryl chloride (Acros, Pittsburgh, Pa.) was purified by distillation at 159–161° C. Propylene glycol was also obtained from Acros and used as received. Anhydrous potassium carbonate (Fisher, Pittsburgh, Pa.) was ground into a fine powder with a mortar and pestle. The solvents for polymer purification were purchased from Fisher as reagent grade and used as received.

Oligomer preparation. Fumaryl chloride, propylene glycol, and potassium carbonate were measured out in a 1:3:1.5 molar ratio. The propylene glycol was dissolved in chloroform (1:2 by volume) and placed in a 2 L-3 neck flask along with the powdered potassium carbonate. This mixture was stirred with an overhead mechanical stirrer to form a slurry. Fumaryl chloride dissolved in chloroform (1:1 volume ratio) was added dropwise to the slurry. The reaction mixture was maintained at room temperature (by altering the rate of the fumaryl chloride addition) under a nitrogen blanket. Additional chloroform was added as needed to facilitate stirring. Upon completion of the fumaryl chloride addition, the mixture was transferred to 50 mL centrifuge tubes and spun down for 15 minutes at 4000 rpm until the potassium carbonate was completely removed. The supernatant was then added dropwise to petroleum ether to force the oligomer out of solution, and the precipitate was rotary-evaporated to yield an amber-colored oil. Transesterification. The oligomer was transferred to a 1 L-3 neck reaction vessel suspended in an oil bath. The bath temperature was raised to 160° C. and the system was evacuated to a pressure of 100–110 mm Hg. Nitrogen was passed through a coil in the oil bath for preheating and subsequently bubbled into the bottom of the reaction vessel to facilitate mixing and maintain an inert environment. Propylene glycol was liberated by the formation of each O—CO bond during the transesterification and was condensed as a byproduct. Samples for kinetic analysis of the molecular weight progression were removed each hour during the reaction. Upon termination of the transesterification, the vessel was pressurized to 1 atm and the product was allowed to cool. This product was dissolved in chloroform and precipitated through dropwise addition of the mixture to petroleum ether with stirring. The precipitate was rotary-evaporated for 2 hours. The final product, PPF, was a much darker color and of a greater viscosity when compared to PPF synthesized in the absence of potassium carbonate. Moreover, the transesterification reaction no longer catalytic antimony trioxide, an undesirable compound for in vivo applications. For the polymer characterization described below, PPF prepared from a 16 hour transesterification with a number average molecular weight of approximately 5000 Da was used.

Polymer Characterization

FTIR Fourier transform infrared spectra were obtained on a Nicolet 500 spectrometer (Madison, Wis.). Samples were placed on a zinc selenide attenuated total reflection crystal for analysis. A total of 32 scans was collected at a 4 cm$^{-1}$ resolution. The peak at 2300 cm$^{-1}$ is due to the presence of carbon dioxide in the sampling chamber.

NMR Nuclear magnetic resonance spectra were obtained on a Bruker 500 MHz spectrometer (Switzerland). $^1$H, Distortionless Enhancement by Polarization Transfer-135 $^{13}$C (DEPT-135 $^{13}$C), and 2D $^1$H-$^{13}$C chemical shift correlation spectra of PPF were acquired using standard pulse programs.

MS Mass spectral data of the oligomer and high molecular weight polymer were obtained in fast-atom bombardment (FAB) mode on a Finnigan MAT 95 spectrometer (New York, N.Y.) using a Cs ion gun. Nitrobenzyl alcohol was used as a matrix.

GPC Gel permeation chromatography was used to determine polymer molecular weight distributions through the application of a differential refractometer detector (Waters, Model 410, Milford, Mass.). A Phenogel guard column (50×7.8 mm, 5 µm, mixed bed, Phenomenex, Torrance, Calif.) and a Phenogel column (300×7.8 mm, 5 µm, mixed bed, Phenomenex) were used to elute the samples at 1 mL/min chloroform flow rate. Polystyrene standards were used to obtain a calibration curve for calculating the polymer molecular weights. Samples were analyzed for four transesterification reactions, each spanning a 16 hour time frame.

Results

Figure 3:
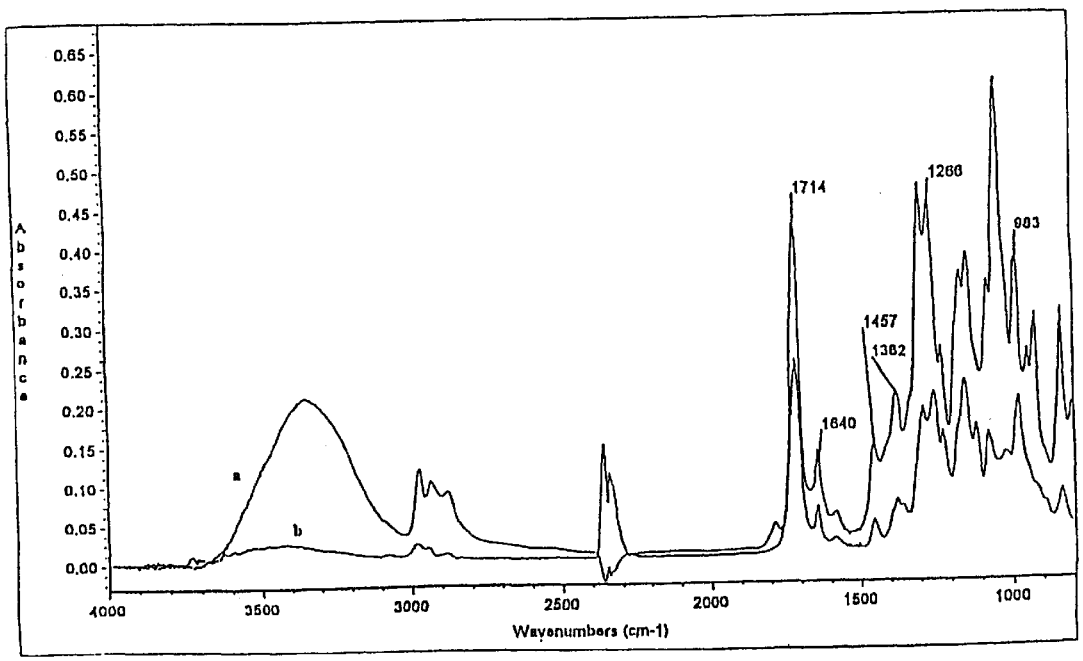
FIG. 3 is an FTIR spectra of poly(propylene fumarate) following transesterification and of the short chain oligomer prior to transesterification.

FTIR Carbonyl stretching at 1714 cm$^{-1}$, C=C stretching at 1640 cm$^{-1}$, and methylene scissoring and asymmetric bending at 1457 cm$^{-1}$ were all evident in the FTIR spectra of the oligomer and final polymer (FIG. 3). C—O stretching at 1266 cm$^{-1}$, methyl symmetric bending at 1382 cm$^{-1}$, and the C—H bend of the double bond at 983 cm$^{-1}$ were also present in both spectra. The oligomer had a more intense OH stretch at 3340 cm$^{-1}$ than the higher molecular weight polymer due to the greater number of hydroxyl end groups in the short chain oligomer. The relative intensity of the hydroxyl peak decreased with increasing molecular weight of the samples taken throughout the transesterification. No major differences were identified in the FTIR spectra of the PPF formed through the new reaction pathway as opposed to the previous method.

NMR Through the combination of proton, carbon, and two-dimensional proton-carbon chemical shift correlation spectra, the PPF chemical structure represented in FIG. 1 was verified. Contour positions for all pertinent functional groups represented in this structure are given in Table 1 and shown in FIGS. 4(a)–(c).

TABLE 1

Identification of Functional Group Contours
From the 2-d Proton-Carbon Correlation NMR Spectra.

| Functional Group | Figure Label | Proton (ppm) | Carbon (ppm) | DEPT Peak |
|---|---|---|---|---|
| Propyl methyl | 1 | 1.15–1.51 | 16.05–19.4 | Methyl |
| Propyl methine of 2° alcohol | 2 | 4.08–4.11 | 65.2 | Methine |
| Propyl methylene of 2° alcohol | 3 | 4.03–4.17 | 69.8–70.1 | Methylene |
| Olefinic bonds | 4 | 6.85–6.93 | 132.9–134.4 | no contour |
| propyl methine of 1° alcohol | 5 | 5.0–5.12 | 72.4–73.1 | Methine |

TABLE 1-continued

Identification of Functional Group Contours
From the 2-d Proton-Carbon Correlation NMR Spectra.

| Functional Group | Figure Label | Proton (ppm) | Carbon (ppm) | DEPT Peak |
|---|---|---|---|---|
| propyl methylene of 1° alcohol | 6 | 3.57–3.69 | 64.7 | Methylene |
| C=0 | not shown | — | 165.0–171.8 | no contour |

The peak assignments are based on calculated proton and carbon chemical shifts found from the tabulated values in Silverstein et al.[10] Acylation of propylene glycol to leave a primary alcohol resulted in a methylene peak (6) with signals at $^1$H 3.57–3.69 and $^{13}$C 64.7 and a methine peak (5) with signals at $^1$H 5.0–5.12 and $^{13}$C 72.4–73.1. Acylation of propylene glycol to leave a secondary alcohol resulted in a methylene peak (3) with signals at $^1$H 4.03–4.17 and $^{13}$C 69.8–70.1 and a methine peak (2) with signals at $^1$H 4.08–4.11 and $^{13}$C 65.2. The spectra of the short chain oligomer and the higher molecular weight polymer were investigated to confirm these peak assignments. The secondary alcohol methylene (3) and primary alcohol methine (5) each produced two signals. The signals within each pair were of approximately the same intensity in the oligomer spectrum. However, in the high molecular weight polymer spectrum, one signal from each pair was more intense. The weaker of the two signals was attributed to the polymer end groups, while the stronger signals were assigned to the interior CH and CH$_2$ of the polymer chain. The stronger signals were more deshielded than the weaker ones because the interior species are located between two ester functionalities. Furthermore, integrated $^1$H spectra gave a ratio of double bond hydrogens to methyl protons of 2:3, as expected from the backbone structure. The integrated spectra of P(PF) produced by the previous method showed a ratio of 1:3, verifying loss of polymer unsaturation.

Figure 4A:
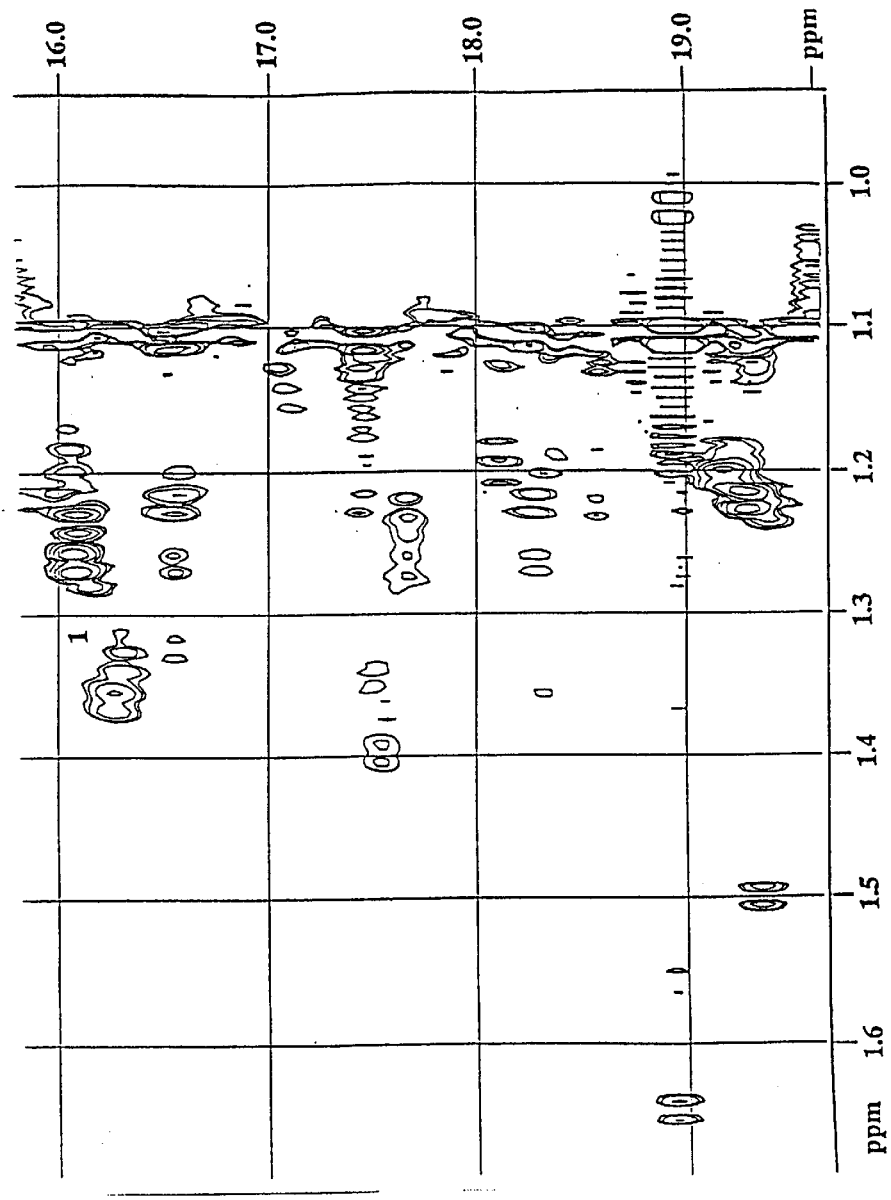
FIGS. 4A–C are a series of NMR spectra confirming the structure illustrated in FIG. 1.
Figure 4B:
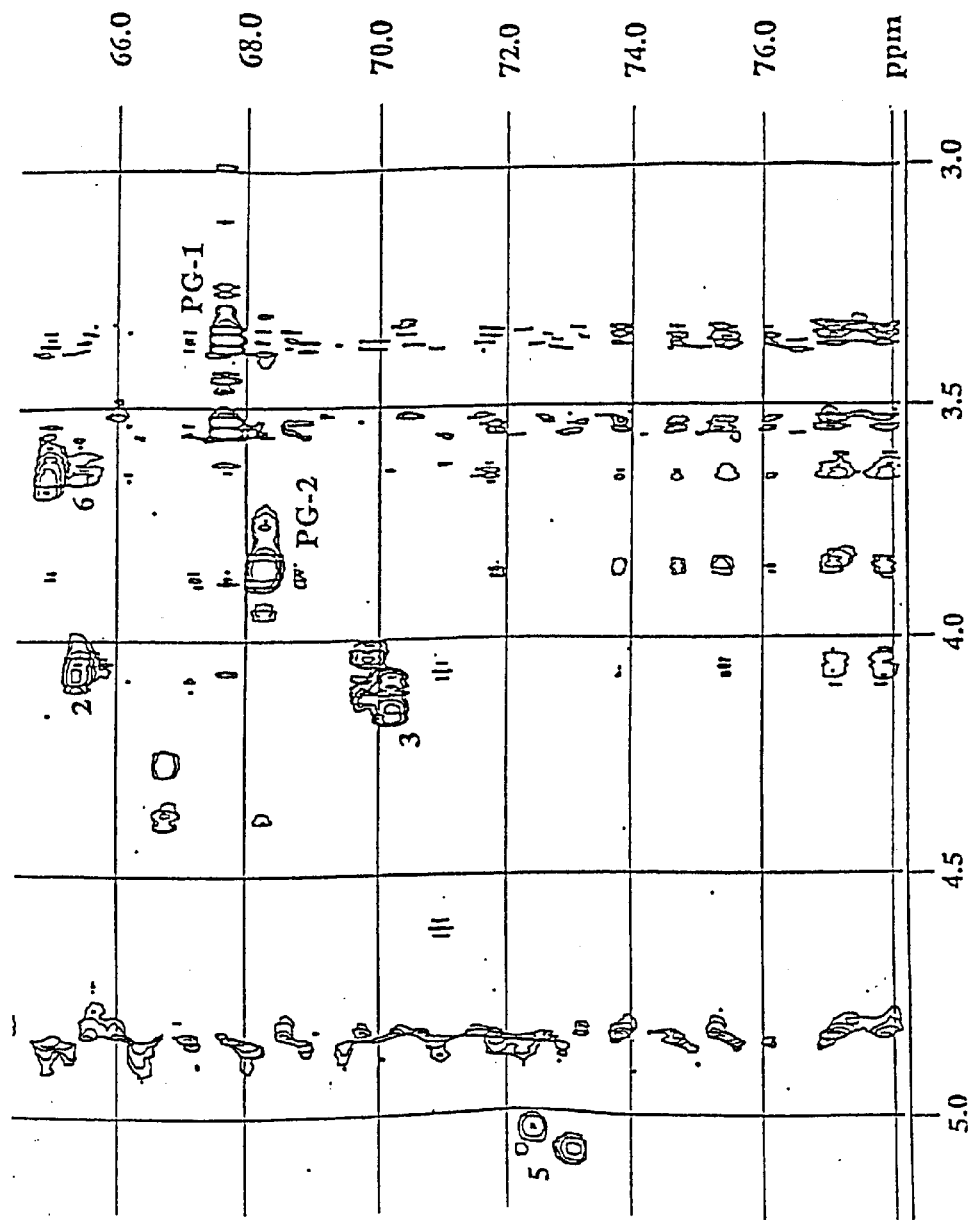
Figure 4C:
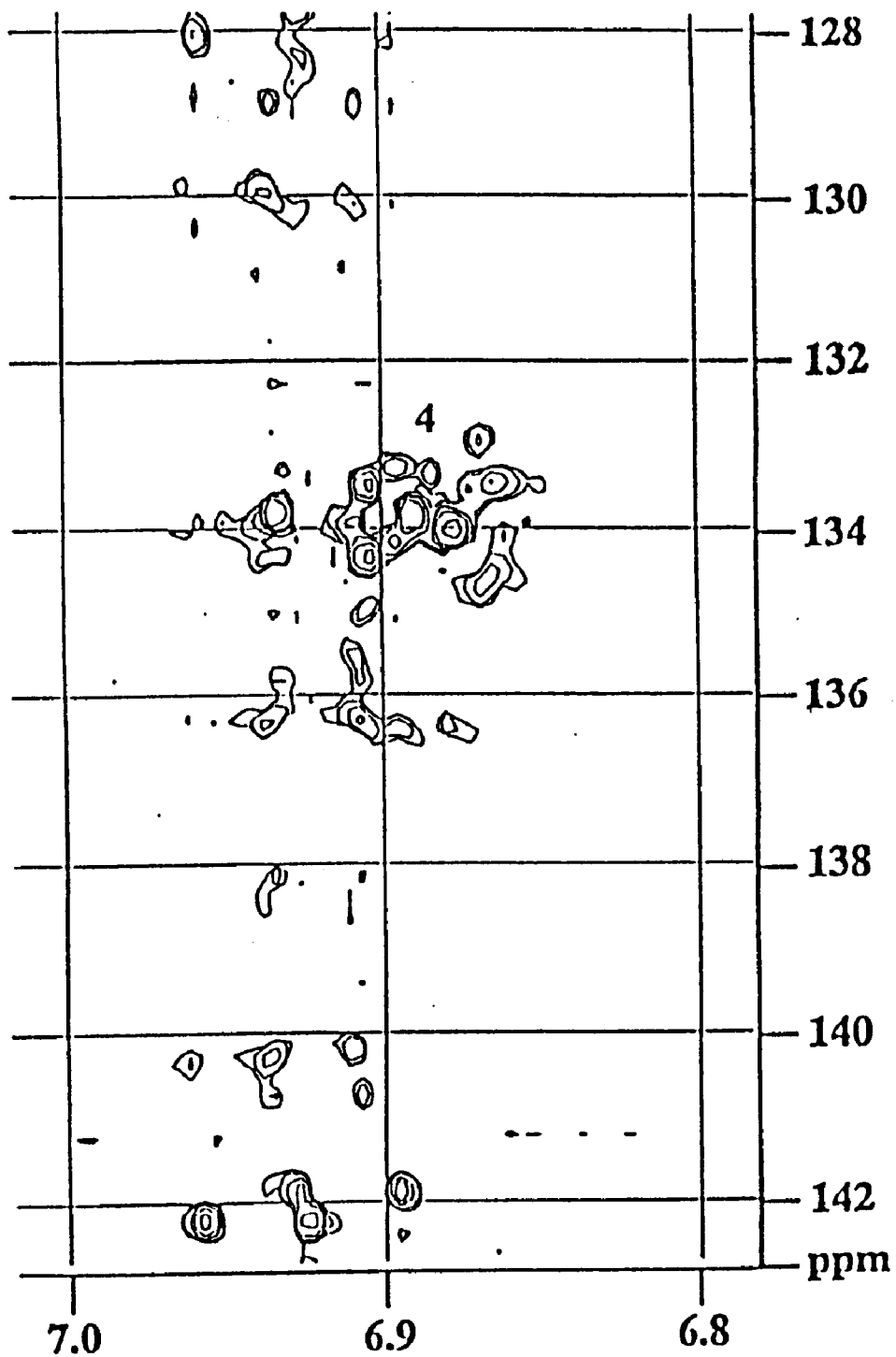

FIG. 4(a) shows the 2-D $^1$H-$^{13}$C coupled NMR spectrum for $^1$H region 1.0–1.5 ppm and $^{13}$C region 15.5–20 ppm. The number 1 corresponds to the methyl functionality labeled in FIG. 1. FIG. 4(b) shows a 2-D $^1$H-$^{13}$C coupled NMR spectrum for $^1$H region 3.0–5.5 ppm and $^{13}$C region 64–74 ppm. The number 2 corresponds to the propyl methine and 3 corresponds to the propyl methylene of the secondary alcohol functionality labeled in FIG. 1, and 5 corresponds to the propyl methine and 6 corresponds to the propyl methylene of the primary alcohol functionality labeled in FIG. 1. The label PG-1 refers to methylene from the residual propylene glycol, and the label PG-2 represents methine from the residual propylene glycol. FIG. 4(c) shows a 2-D $^1$H-$^{13}$C coupled NMR spectrum for $^1$H region 6.8–7.0 ppm and $^{13}$C region 127–143 ppm. The number 4 corresponds to the fumarate double bond atoms as labeled in FIG. 1.

Peaks not attributable to P(PF) and due to residual propylene glycol are present at $^1$H 1.1 ppm and $^{13}$C 18.8–19.0 ppm for the methyl groups, and at $^1$H 3.3–3.5 and 3.8–3.9 ppm and $^{13}$C 67.6–68.2 and 68.2–68.6 ppm, respectively, for the methylene and methine groups.

Major byproducts were identified in the NMR spectra of P(PF) produced by the previous synthetic method. Propylene glycol addition across the double bond led to peaks at 46.5 and 71 ppm, while HCl addition produced additional methylene $^1$H signals at 2.8–3.3 ppm and $^{13}$C signals at 39–40 ppm and methine $^1$H signals at 4.6–4.8 ppm and $^{13}$C signals at 51–52 ppm. Since no evidence of either of these side products was seen in any of the NMR spectra collected in the present study, the addition of $K_2CO_3$ represents a great improvement over the previous synthetic method.

Kinetic studies of the transesterification showed that the molecular weight of a P(PF) reached a final $M_n$ of 4900 (±700) and $M_w$ of 9100 (±1300) after 16 hours, while the polydispersity index remained below 1.8 throughout the reaction. Thus the P(PF) synthesized by the new method is of higher molecular weight and greater purity than previously prepared material having the same formula. According to two dimensional NMR, the backbone structure of this polymer was as expected and contained no byproducts formed by acid catalyzed addition across the fumarate double bond. It is expected that the present technique will have applicability to P(PF) formation reactions regardless of whether those reactions include the use of a catalyst.

In sum, the present invention provides an efficient and reproducible technique for synthesizing P(PF) having a molecular weight above 4,000 and a low polydispersity index. This P(PF) is particularly well suited for use in bone cements. A P(PF)-containing composition that is an effective bone cement is described in detail in application Ser. No. 09/289,361, now U.S. Pat. No. 6,124,373, filed concurrently herewith and entitled Bone Replacement Compound Comprising Poly(Polypropylene Fumarate), which is incorporated by reference herein in its entirety.

While a preferred embodiment has been disclosed and described, it will be understood that certain modifications could be made without departing from the scope of the present invention. For example, the potassium carbonate that serves as an acid neutralizer in the preferred embodiment could be replaced with any suitable proton scavenger, such as but not limited to similar salts, including other alkaline earth and alkali metal carbonates.

As discussed above, the P(PF) made according to the present invention is suitable for use in a replacement compound for living bone. The P(PF) can be incorporated into a paste, along with a monomer capable of addition polymerization an inorganic filler such as beta-tricalcium phosphate, sodium chloride or hydroxyapatite, a radical initiator such as benzoyl peroxide, azobisisobutyronitrile, or acetyl peroxide, and an accelerator such as N,N dimethyl toluidine. Examples of suitable monomer include vinyl pyrrolidone, acrylic acid, methyl methacrylate, styrene, methacrylic acid, or 2-hydroxy ethyl methacrylate, and copolymers thereof. While it is preferred that the monomers used are biodegradable, it is contemplated that non-biodegradable monomers such as methyl methacrylate will form only short polymer chains, which, upon degradation of the poly (propylene fumarate) backbone, in vivo, will be cleared from a patient's body by normal metabolic processes. Various amounts of the specific ingredients may be combined to produce a useful product. For example, approximately equal amounts of the poly(propylene fumarate), monomer, and filler may be used. The amounts of each component may be varied according to the desired characteristics of the final composition, as known to one of skill in the art. Likewise, the amount of initiator and accelerator may be varied by one of skill in the art to produce a composite having desired physical characteristics. Preferably, the components are combined in a sterile field, and pass through a moldable putty stage prior to hardening. In addition, by varying the molecular weight of the poly(propylene fumarate) a composite material having desired strength and modulus characteristics, including that which approximates the physical characteristics of human trabecular bone, is produced.

What is claimed is:

1. Poly(polypropylene fumarate) having a weight average molecular weight above 5,000 and a polydispersity index below 2.0.

2. Poly(polypropylene fumarate) having a weight average molecular weight above 2,000 and a polydispersity index below 2.0.

3. A method for synthesizing poly(polypropylene fumarate), comprising:

(a) reacting fumaryl chloride to form bis(hydroxypropyl fumarate); and (b) transesterifying the bis(hydroxypropyl fumarate);

wherein step (a) is carried out in the presence of a proton scavenger.

4. The method of claim 3 wherein the proton scavenger is selected from the group comprising amines, buffers and carbonate salts.

5. The method of claim 3 wherein the proton scavenger is selected from the group comprising alkali metal carbonates and alkaline-earth metal carbonates.

6. The method of claim 3 wherein the proton scavenger is potassium carbonate.

7. The method of claim 3 wherein step (b) produces poly(polypropylene fumarate) having a weight average molecular weight above 5,000 and a polydispersity index below 2.0.

8. The method of claim 3 wherein step (b) produces poly(polypropylene fumarate) having a weight average molecular weight above 9,000 and a polydispersity index below 2.0.

9. A composition suitable for use in orthopedic applications, comprising:

poly(propylene fumarate);

a monomer capable of addition polymerization;

an inorganic filler; and a radical initiator; and wherein said poly(propylene fumarate) has a weight average molecular weight above 5,000 and a polydispersity index below 2.0.

10. The composition according to claim 9 wherein said monomer is selected from the group consisting of vinyl pyrrolidone, acrylic acid, methyl methacrylate, styrene, methacrylic acid, 2-hydroxy ethyl methacrylate, and copolymers thereof.

11. The composition according to claim 9 wherein said inorganic filler is selected from the group consisting of beta-tricalcium phosphate, sodium chloride, hydroxyapatite and combinations thereof.

12. The composition according to claim 9 wherein said radical initiator is selected from the group consisting of such as benzoyl peroxide, azobisisobutyronitrile, and acetyl peroxide.

13. The composition according to claim 9 wherein said poly(propylene fumarate) has a weight average molecular weight above 9,000 and a polydispersity index below 2.0.

14. The composition according to claim 13 wherein said composition includes an amount of cross linking agent between about 0.25 ml per gram of P(PF) and about 0.5 ml per gram of P(PF).

15. The composition according to claim 13 wherein said composition includes an amount of initiator between about 0.001 grams per gram of P(PF) and about 0.005 grams per gram of P(PF).

16. The composition according to claim 13, further including an accelerator.

17. A method for synthesizing poly(polypropylene fumarate), comprising:
   (a) reacting fumaryl chloride to form bis(hydroxypropyl fumarate);
   (b) transesterifying the bis(hydroxypropyl fumarate); and
   (c) substantially maintaining the unsaturation of the fumarate.

18. The method of claim 16, including the step of carrying out step (a) in the presence of a proton scavenger.

19. The method of claim 17 wherein the proton scavenger is selected from the group comprising alkali metal carbonates and alkaline-earth metal carbonates.

20. The method of claim 18 wherein the proton scavenger is potassium carbonate.

21. The method of claim 16 wherein step (b) produces poly(polypropylene fumarate) having a weight average molecular weight above 5,000 and a polydispersity index below 2.0.

22. The method of claim 16 wherein step (b) produces poly(polypropylene fumarate) having a weight average molecular weight above 9,000 and a polydispersity index below 2.0.

* * * * *

UNITED STATES PATENT AND TRADEMARK OFFICE
CERTIFICATE OF CORRECTION

PATENT NO.    : 6,355,755 B1
DATED         : March 12, 2002
INVENTOR(S)   : Peters, Susan J., Suggs, Laura J., Engel, Paul S. and Mikos, Antonios G.

It is certified that error appears in the above-identified patent and that said Letters Patent is hereby corrected as shown below:

<u>Columns 8, 9 and 10,</u>
In each of claims 1-3, 7, 8, 17, 21 and 22, replace "poly(polypropylene fumarate)" with -- poly(propylene fumarate). --

Signed and Sealed this

Fifteenth Day of October, 2002

*Attest:*

JAMES E. ROGAN
*Attesting Officer*              *Director of the United States Patent and Trademark Office*